United States Patent
Nakahira et al.

(10) Patent No.: US 9,360,434 B2
(45) Date of Patent: Jun. 7, 2016

(54) OPTICAL INSPECTION APPARATUS AND METHOD THEREOF

(71) Applicant: Hitachi, Ltd., Chiyoda-ku, Tokyo (JP)

(72) Inventors: Kenji Nakahira, Tokyo (JP); Toshifumi Honda, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/378,478

(22) PCT Filed: Feb. 12, 2013

(86) PCT No.: PCT/JP2013/053177
§ 371 (c)(1),
(2) Date: Aug. 13, 2014

(87) PCT Pub. No.: WO2013/145898
PCT Pub. Date: Oct. 3, 2013

(65) Prior Publication Data
US 2015/0015893 A1 Jan. 15, 2015

(30) Foreign Application Priority Data
Mar. 27, 2012 (JP) ................................. 2012-070542

(51) Int. Cl.
*G01B 9/02* (2006.01)
*G01N 21/88* (2006.01)
(Continued)

(52) U.S. Cl.
CPC ................ *G01N 21/88* (2013.01); *G01N 21/21* (2013.01); *G01N 21/45* (2013.01);
(Continued)

(58) Field of Classification Search
CPC ............. G01B 9/0209; G01B 9/02091; G01B 11/2441; G01N 21/4795; G01N 21/21; G01N 21/88; G01N 21/95607; G01N 21/8851; G06T 7/0004; G06T 7/0008
See application file for complete search history.

(56) References Cited

U.S. PATENT DOCUMENTS 4,764,013 A * 8/1988 Johnston ................. 356/484
5,214,282 A * 5/1993 Yamaguchi et al. ......... 850/16
(Continued)

FOREIGN PATENT DOCUMENTS

| JP | 63-200042 A | 8/1988 |
|---|---|---|
| JP | 6-194320 A | 7/1994 |

(Continued)

OTHER PUBLICATIONS

B. Cretin "Measurement of cantilever vibrations with a new heterodyne laser probe: application to scanning microdeformation microscopy", Oct. 1, 1997.*
(Continued)

*Primary Examiner* — Michael A Lyons
*Assistant Examiner* — Maurice Smith
(74) *Attorney, Agent, or Firm* — Crowell & Moring LLP

(57) ABSTRACT

An object of the present invention is to provide an optical inspection apparatus that suppresses an influence of quantum noise and obtains superior defect detection performance even when an amount of light is small and a method thereof.
In order to resolve the above problem, the present invention provides an optical inspection apparatus that includes a light source which radiates light to a sample; a light interference device which causes target light transmitted, scattered, or reflected from the sample and reference light to interfere with each other, such that strength of light after the interference becomes lower than strength of the target light; a photon counter which measures a photon number of the light after the interference by the light interference device; and a defect identifier which identifies the presence or absence of a defect, on the basis of a detected photon number obtained by the photon counter.

16 Claims, 15 Drawing Sheets

(51) Int. Cl.
*G06T 7/00* (2006.01)
*G01N 21/21* (2006.01)
*G01N 21/45* (2006.01)
*G01N 21/84* (2006.01)
*G01N 21/95* (2006.01)
*G01N 21/94* (2006.01)

(52) U.S. Cl.
CPC ....... *G01N 21/8422* (2013.01); *G01N 21/8806* (2013.01); *G01N 21/94* (2013.01); *G01N 21/95* (2013.01); *G06T 7/0008* (2013.01); *G01N 2201/0697* (2013.01); *G01N 2201/0698* (2013.01); *G01N 2201/06113* (2013.01)

(56) References Cited

U.S. PATENT DOCUMENTS

| | | | | |
|---|---|---|---|---|
| 5,486,919 A | * | 1/1996 | Tsuji et al. | 356/484 |
| 5,883,714 A | * | 3/1999 | Jann et al. | 356/484 |
| 5,892,583 A | * | 4/1999 | Li | 356/479 |
| 6,018,391 A | * | 1/2000 | Yoshida | 356/484 |
| 7,823,215 B2 | * | 10/2010 | Giakos | 850/31 |
| 2002/0159052 A1 | * | 10/2002 | Klooster et al. | 356/237.2 |
| 2011/0063621 A1 | | 3/2011 | Konno | |

FOREIGN PATENT DOCUMENTS

| | | |
|---|---|---|
| JP | 9-304289 A | 11/1997 |
| JP | 10-185782 A | 7/1998 |
| JP | 2006-201179 A | 8/2006 |
| JP | 2011-85569 A | 4/2011 |

OTHER PUBLICATIONS

Yan Chen, "Dual-Color Photon-Counting Histogram", Biophysical Journal vol. 88, Mar. 2005.*
Kanseri, Bhaskar, "Mathematicalformulationforverificationofthe Fresneland Arago interferencelawsusingaMach-Zehnderinterferometer", Direct Science, Jul. 24, 2008.*
B. Leslie, "Statistical Aspects of Surface Particle Counting", Plenum Press 1991.*
K. Yamamoto, "Development of Multi-Pixel Photon Counter", IEEE Nov. 17, 2006.*
Kanseri, Bhaskar, "Mathematical formulation for verification of the Fresnel and Arago interference laws using a Mach-Zehnder interferometer", Direct Science, Jul. 24, 2008.*
International Search Report (PCT/ISA/210) dated Apr. 2, 2013, with English translation(Four (4) pages).

* cited by examiner

OPTICAL INSPECTION APPARATUS AND METHOD THEREOF

TECHNICAL FIELD

The present invention relates to an optical inspection apparatus and a method thereof.

BACKGROUND ART

In manufacturing lines of semiconductor substrates and thin film substrates, optical inspection apparatuses that inspect a minute defect present on a surface of a sample have been widely used to obtain a high yield of products (for example, see PTLS 1 and 2). Generally, an optical inspection apparatus radiates light condensed at a width of several-ten μm to the surface of the sample, condenses/detects light (hereinafter, referred to as the target light) transmitted, scattered, or reflected from a defect, and performs defect detection. An apparatus that is put to practical use at the present time can inspect a defect of several-ten nm or more.

CITATION LIST

Patent Literatures

PTL 1: JP 9-304289 A
PTL 2: JP 2006-201179 A

SUMMARY OF INVENTION

Technical Problem

Here, with the development of fine processing technology, there has been a growing demand for inspecting a minuter defect. In the minute defect, because light obtained from the defect is weak, high-performance defect detection technology that can be applied to the weak light is necessary. In particular, because an influence of inevitable fluctuation based on the uncertainty principle of quantum mechanics to be called quantum noise cannot be ignored in the weak light, it becomes important to suppress an influence of the quantum noise.

As a method of inspecting the defect, a method of identifying the presence or absence of the defect, on the basis of information regarding an amplitude difference/phase difference of light obtained from a sample and reference light, like homodyne detection or heterodyne detection, is known.

In the optical inspection apparatuses described in PTLs 1 and 2, after light obtained by causing the target light and the reference light to interfere with each other is converted into an electrical signal by a detector, defect detection is performed on the obtained electrical signal. At this time, according to the quantum mechanics, because the influence of the quantum noise cannot be essentially suppressed after the light is detected by the detector, a process for suppressing the influence of the quantum noise before the detection is necessary. However, in the apparatuses according to the related art, no device is made to suppress the influence of quantum noise in the interference with the reference light. For this reason, if an amount of light is small, superior defect detection performance is not obtained.

The present invention has been made in view of the above-described circumstances and an object of the present invention is to provide an optical inspection apparatus that suppresses an influence of quantum noise and obtains superior defect detection performance even when an amount of light is small and a reception method thereof.

Solution to Problem

In order to solve the above-described problem, according to the present invention, there is provided an optical inspection apparatus, including: a light source which radiates light to a sample; a light interference device which causes target light transmitted, scattered, or reflected from the sample and reference light to interfere with each other, such that strength of light after the interference becomes lower than strength of the target light; a photon counter which measures a photon number of the light after the interference by the light interference device; and a defect identifier which identifies the presence or absence of a defect, on the basis of a detected photon number obtained by the photon counter.

Further, according to the present invention, there is provided an optical inspection method, including: a light radiation step of radiating light to a sample; a light interference step of causing target light transmitted, scattered, or reflected from the sample and reference light to interfere with each other, such that strength of light after the interference becomes lower than strength of the target light; a photon count step of measuring a photon number of the light after the interference; and a defect identification step of identifying the presence or absence of a defect, on the basis of a detected photon number obtained by the photon count step.

Advantageous Effects of Invention

According to the present invention, an optical inspection apparatus that suppresses an influence of quantum noise and obtains superior defect detection performance even when an amount of light is small and a method thereof can be provided.

DESCRIPTION OF EMBODIMENTS

Hereinafter, embodiments of the present invention will be described using the drawings.

First Embodiment

Figure 1:
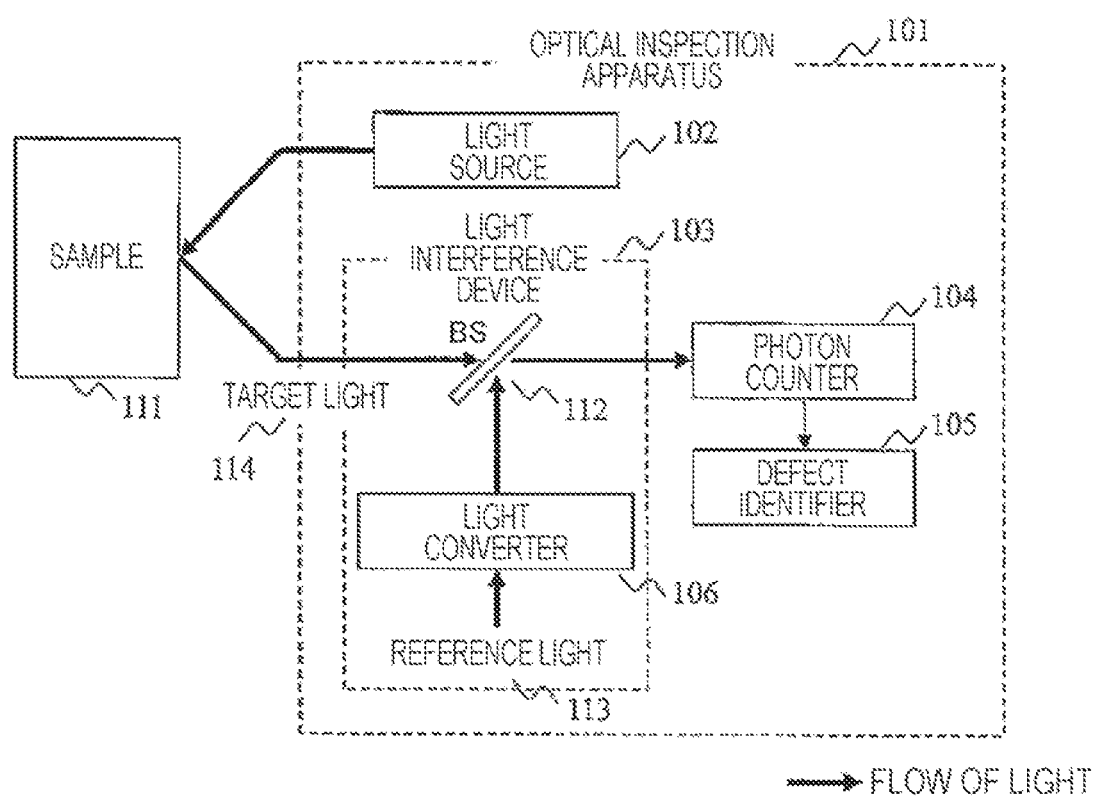
FIG. 1 is a structural diagram of an optical inspection apparatus according to a first embodiment.

An optical inspection apparatus according to a first embodiment of the present invention that radiates light to a sample and inspects a minute defect present on a surface of a sample will be described using FIG. 1. This embodiment includes a light source 102 that radiates light to a sample 111, a light interference device 103 that causes target light 114 transmitted, scattered, or reflected from the sample 111 to interfere with reference light 113, such that amplitude of light after the interference becomes smaller than amplitude of the target light in at least one of the case in which a defect is present and the case in which a defect is absent, a photon counter 104 that measures a photon number of the light after the interference by the light interference device 103, and a defect identifier 105 that identifies the presence or absence of the defect, on the basis of a detected photon number obtained by the photon counter 104.

An optical inspection apparatus 101 includes the light source 102 that radiates light to the sample 111, the light interference device 103 that causes light scattered or reflected from the sample to interfere with the reference light 113, the photon counter 104 that counts a photon number of light after the interference, and the defect identifier 105 that identifies the presence or absence of a defect using a detected photon number. Generally, the light radiated to the sample 111 is condensed on the sample 111 to enhance space resolution and a surface of the sample 111 is scanned with the condensed light. However, the present invention is not limited thereto. The light interference device 103 causes light to interfere with other light, using a beam splitter (in the drawings, referred to as BS) 112 or a polariscope. In addition, the light interference device 103 has a light converter 106 to convert light, such that overlapping of probability distributions regarding the detected photon number is minimized in the case in which a defect is present and in the case in which a defect is absent, as described below using FIG. 9. The light converter 106 generates reference light in which amplitude and a phase of the reference light 113 have been controlled and inputs the reference light to the beam splitter 112.

As such, after the strength (amplitude) of the light is decreased by the interference with the reference light in which the amplitude and the phase have been controlled, as compared with the strength of the light before the interference, a photon count is performed, so that an influence of quantum noise can be suppressed and defect detection sensitivity can be improved (or an inspection time is decreased after the defect detection sensitivity is maintained), as described below using FIGS. 7A to 7C and 9.

In addition, in the light source 102, appropriate light may be radiated according to purposes or inspection conditions. For example, the light may be laser light having a single oscillation frequency or may have multiple oscillation frequencies. Also, the light may be pulse light to be intermittent light or may be continuous light. A state of the light may be polarized or any one of amplitude, a phase, or a frequency of the light may be modulated. Also, the light may be light of a coherent state to be a state of normal laser light, may be light of a squeezed state, or may be light of a photon number state.

The target light is not limited to the light scattered or reflected from the sample and may be light transmitted from the sample. The light interference device may not only cause the light to interfere with one type of reference light but also cause the light to interfere with two types or more of reference light. The type of the reference light may not be the same as the type of the light radiated to the sample. For example, as described below using FIGS. 6A and 6B, the light source 102 radiates light of a coherent state and light of a squeezed state may be used as the reference light 113. The beam splitter may not be used at the time of the interference with the reference light. For example, the interference may be performed using a polarization plate. A detected photon number to be an output of the photon counter 104 is normally an electrical signal. The defect identifier 105 identifies the presence or absence of the defect by an analog or digital electrical circuit. The interference and the photon count may be performed for light (for example, linear light) of a plurality of space modes. This case can be realized by using a line sensor as a photon counter. If the light of the plurality of space modes is used, light is radiated to a wide space of the sample and the presence or absence of the defect can be identified in parallel for individual small spaces obtained by dividing the space into some spaces.

Figure 5A:
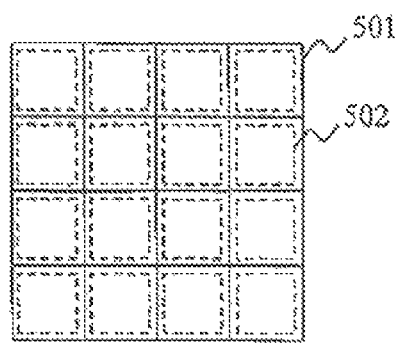
FIG. 5A is a structural diagram of a photon counter according to the first embodiment.
Figure 5B:
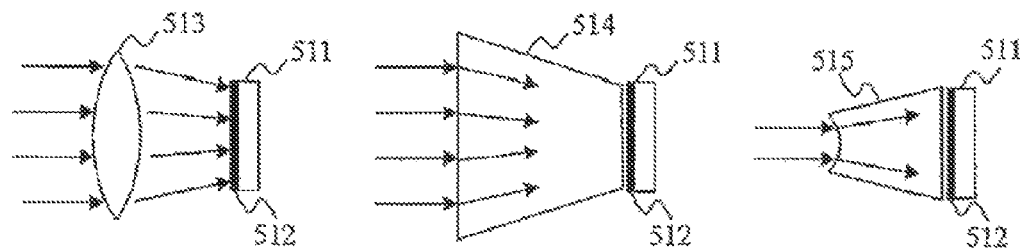
FIG. 5B is a structural diagram of a photon counter according to the first embodiment.

FIGS. 5A and 5B illustrate the photon counter 104 according to this embodiment. When the photon count is performed, it is necessary to use the photon counter 104 in which quantum efficiency is high, a dark count rate is low, and a response speed is sufficient. Here, the quantum efficiency is a rate at which the photon counter can accurately count the photons arriving at the photon counter and the dark count rate is a rate at which the photon counter counts the photons (that is, the photon counter performs erroneous detection), even though the photons do not arrive. As the photon detector 104 in which the quantum efficiency is high and the dark count rate is low, a Geiger mode/avalanche photodiode or a photomultiplier is exemplified. However, when the photon detector 104 is used as a single body, a response speed is not sufficiently high. Therefore, the plurality of photon detectors 104 are used and light reception surfaces 502 corresponding to the photon detectors 104 are arranged in a two-dimensional lattice shape like 501. In addition, a multi-pixel photon counter that is put to practical use in recent years may be used. As such, in this embodiment, in the photon counter 104, any one of a plurality of Geiger mode/avalanche photodiodes, a plurality of photomultipliers, and a multi-pixel photon counter is used. A spot size of the interference light is adjusted such that the entire interference light is made to shine on the light reception surfaces and the interference light shines on as many light reception surfaces as possible.

As such, any one of the plurality of Geiger mode/avalanche photodiodes, the plurality of photomultipliers, and the multi-pixel photon counter is used, so that the quantum efficiency, the dark count rate, and the response speed can be realized at the same time. The photon count is performed on the interference light by the photon counter 194, so that high defect detection performance can be realized.

FIG. 5B illustrates an example of the photon counter 104 in which a lens is arranged on a front step of a light detector 511 to accurately guide the interference light to a light reception surface 512. When a spot size of the interference light is large for the light reception surface 512 of the light detector 511, after a convex lens 513 is arranged on a front surface of the light reception surface 512 to decrease the spot size of the interference light, the interference light is input to the light detector 511. In addition, the spot size may be decreased using a light guide 514. In contrast, when the spot size of the interference light is small for the light reception surface 512, the spot size may be increased using a light guide 515. Instead of the light guides 514 and 515, a concave lens may be used. Shapes of the light guides 514 and 515 are designed such that the interference light accurately shines on the light reception surface 512. Instead of simple shapes, the light guides 514 and 515 may have complex shapes. For example, input sides of the light guides 514 and 515 may have circular shapes and output sides of the light guides 514 and 515 may have square shapes to allow light to efficiently shine on the light reception surface 501 of the light detector. In addition, the light reception surface 501 of the light detector does not need to have a square shape and may have a shape (for example, a circular shape) in which the light guides 514 and 515 are easily designed.

Figure 19:
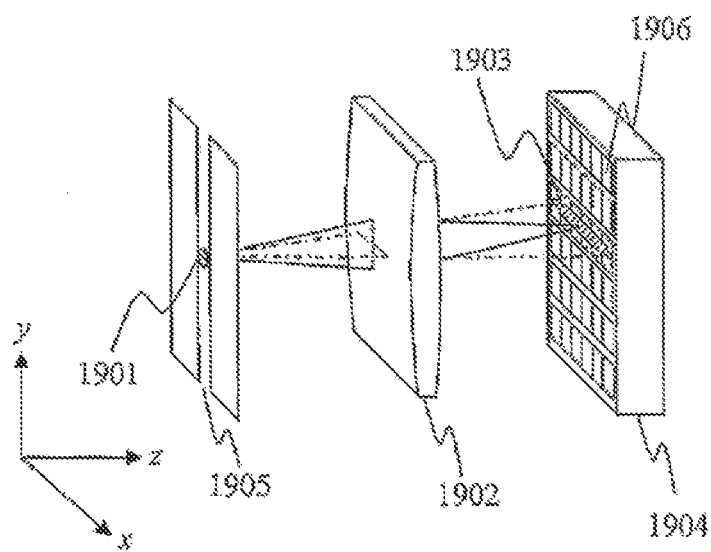
FIG. 19 is a diagram illustrating an optical counter according to a first modification of the first embodiment.

FIG. 19 illustrates a photon counter according to a first modification of this embodiment. The modification illustrated in FIG. 19 includes a slit 1905, a lens 1902, and a photon counter 1904. The photon counter 1904 includes a plurality of photon detectors 1906. In the photon counter 1904, any one of a plurality of Geiger mode/avalanche photodiodes, a plurality of photomultipliers, and a multi-pixel photon counter can be used. When light passes through the slit 1905 extended in a y direction, the light is diffracted in an x direction. The lens 1902 is flat with respect to the x direction, but convex with respect to the y direction and performs a function of condensing a y component of light. As a result, light 1901 takes a distribution in which the light does not diffuse in the y direction and diffuses in the x direction, like a region 1903, in the light reception surface of the photon counter 1904. Thereby, the photon count can be performed on each y component, using the plurality of photon detectors arranged in the x direction. According to the first modification of this embodiment, the photon counter 1904 can be used as a line sensor in which six photon counters are arranged in the y direction. For this reason, the photon count can be performed simultaneously with respect to light of a plurality of space modes diffused in the y direction. As a mechanism for diffusing the light in the x direction, instead of the slit 1905, a concave lens or a lens diffusion plate may be used.

Figure 20:
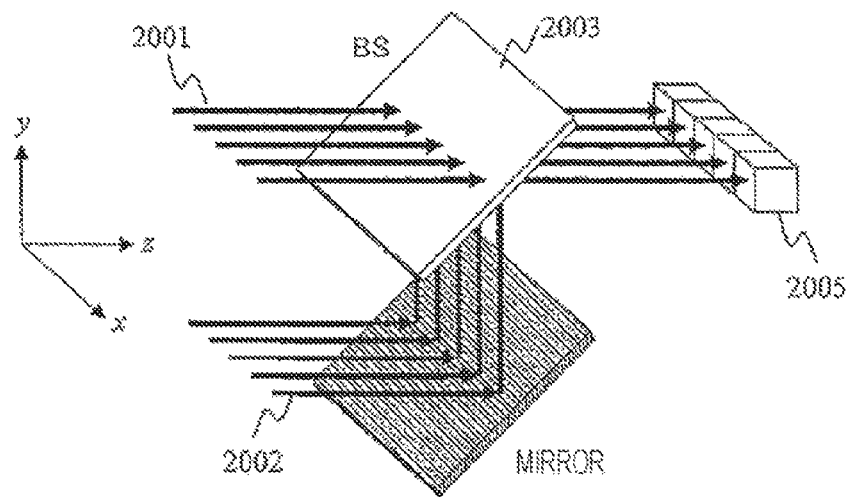
FIG. 20 is a diagram illustrating an optical counter according to a second modification of the first embodiment.

FIG. 20 illustrates a photon counter according to a second embodiment of this embodiment. A BS 2003 is an example of the BS 112 in FIG. 1 and a line sensor 2005 is an example of the photon counter 104. In the line sensor 2005, the configuration described with reference to FIG. 19 can be used (however, in an example of the drawing, it is necessary to use the line sensor after the line sensor is rotated around a z axis by 90 degrees). The BS 2003 causes target light 2001 to interfere with reference light 2002 in which an amplitude/phase has been controlled and a photon number of light after the interference is counted using the line sensor 2005. From the line sensor 2005, a detected photon number from each sensor is output. The defect identifier identifies the presence or absence of a defect for each space mode, on the basis of each detected photon number.

According to the first and second modifications of this embodiment, even when the defect inspection is performed in parallel using the line sensor, in each defect inspection, the photon count is performed after the interference with the reference light in which the amplitude and the phase have been controlled is performed, so that an influence of quantum noise can be suppressed.

A relation of phases and amplitudes of target light and interference light in the case in which a defect is absent and in the case in which a defect is present will be described using FIGS. 7A to 7C.

Figure 7A:
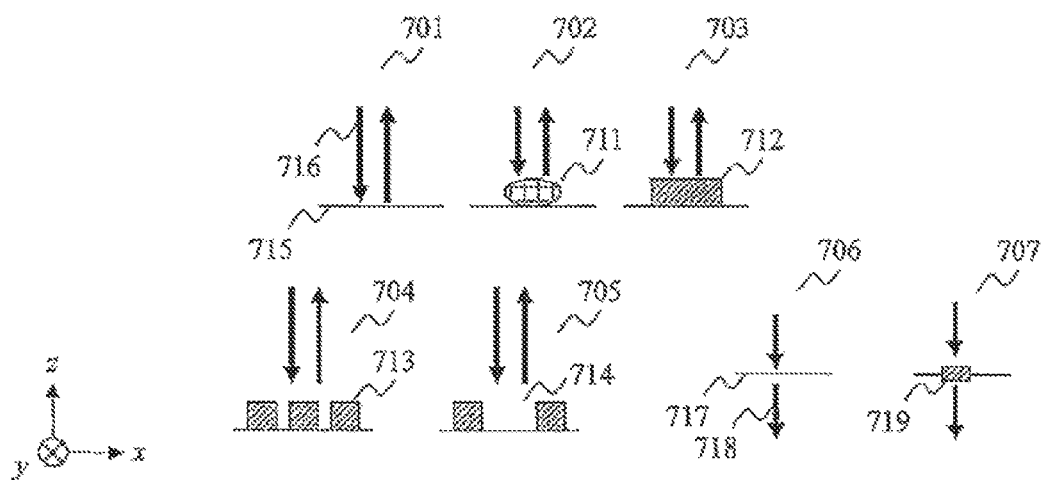
FIG. 7A is a diagram illustrating a representative example of a defect according to the first embodiment.

FIG. 7A illustrates an example of a shape or a type of a defect. An example of a sample 715 at a position where a defect is absent is represented by 701. An arrow 716 represents radiation light and target light. An example of a sample including a defect 711 is represented by 702. The radiation light shines on the defect or scattered light or reflected light from the defect is generated. Because an optical path length is different by a height of the defect as compared with the case of 701, a phase of the target light is different from a phase in the case of 701. An example of a sample including a defect 712 having the same height as the defect 711 is represented by 703. Because the height of the defect is the same, an optical path length is the same. However, if a type or a shape of a sample is different, an aspect of an interaction of the sample and the light changes. For this reason, amplitude or a phase of the target light generally changes. An example of a sample 713 different from the example of 701 at the position where a defect is absent is represented by 704. In this example, the sample 713 has unevenness even in a state in which a defect is absent. An example of the case in which the sample 713 includes a defect 714 is represented by 705. A part of the sample 713 is notched and this is a type of a defect. As compared with the sample 713 in which a defect is absent, because the optical path length or the interaction of the sample and the light is different, this affects the amplitude or the phase of the target light.

An example of a sample 717 at a position where a defect is absent is represented by 706. In this example, transmitted light from the sample is set as target light 718. An example of a sample including a defect 719 is represented by 707. By the defect 719, a state of the transmitted light is changed. According to a sample to be inspected or a type of a defect, which of transmitted light from the sample and scattered light or reflected light is set as target light is changed. However, in all cases, a state of the target light changes in the case in which a defect is present and in the case in which a defect is absent and if the change thereof can be detected, the presence or absence of the defect can be identified.

Figure 7B:
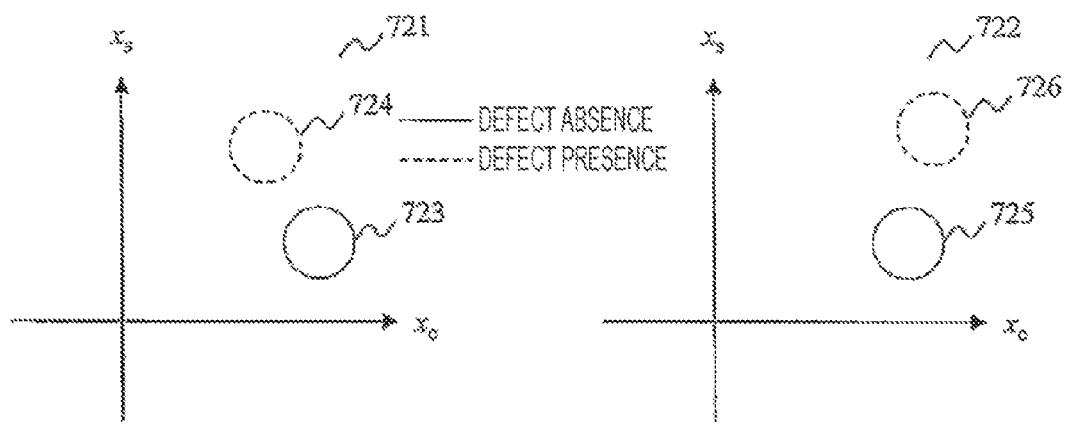
FIG. 7B is a diagram representing a state of target light according to the first embodiment by a phase space representation.
Figure 7C:
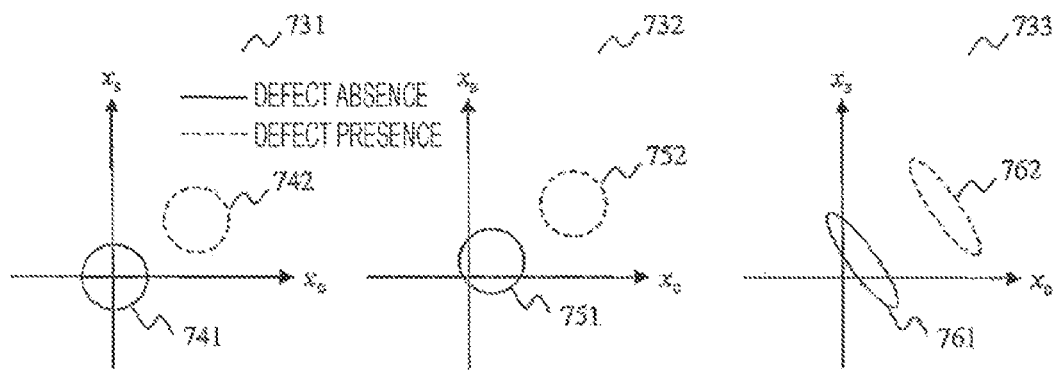
FIG. 7C is a diagram representing a state of interference light according to the first embodiment by a phase space representation.

FIGS. 7B and 7C illustrate examples of phase space representations representing states of target light and interference light, respectively. In these drawings, a distance from an original point (point becoming $x_c=x_s=0$) represents amplitude of light and an angle with an x, axis (horizontal axis) represents a phase of the light. If noise is not overlapped and amplitude or a phase is only a determined value, the state of the light is represented by one point in the phase space representation. In actuality, however, because quantum noise is inevitably overlapped, the amplitude/phase is uncertain. Therefore, the state of the light having the uncertainty is represented by a probability density distribution for a two-dimensional space represented by the ($x_c$, $x_s$) coordinates. Here, a set of states in which the probabilities become equal to or more than constant values is illustrated in a circle or an elliptical circle. Average values of the amplitudes and the phases having the uncertainty are called the amplitude and the phase, respectively. A region 723 of a graph 721 in FIG. 7B represents a state of target light in the case in which a defect is absent (for example, the case of 701). A region 724 represents a state of the case in which a defect is present (for example, the case of 702). As compared with the region 723, the amplitude of the target light is the same, but the phase is different. A region 725 of a graph 722 represents a state of the case in which a defect is absent, similar to the region 723. Meanwhile, a region 726 represents a state of the case in which a defect different from the defect of the region 724 is present (for example, the case of 703). As compared with the region 725, both the phase and the amplitude of the target light are different.

FIG. 7C illustrates a state of interference light corresponding to the target light illustrated by the graph 721 or 722. By interference with reference light, it is possible to perform the position shift of a constant amount for the target light of the graph 721 or 722 on a two-dimensional graph illustrated by a phase space representation, as illustrated by a graph 731 or 732. In order to simplify the description, in these graphs, rotation around the original point is also performed. When the photon count is performed after the interference, amplitude in the graphs is measured. For this reason, a rotation operation does not affect a detected photon number to be a measurement result.

The position shift amounts for the $x_c$ axis and the $x_s$ axis can be controlled by the amplitude and the phase of the reference light. When the target light and the reference light are light of a coherent state having amplitudes/phases to be represented by ($a_c$, $a_s$) and ($b_c$, $b_s$) at the ($x_c$, $x_s$) coordinates, respectively, the interference light after the interference using the beam splitter becomes light of a coherent state having an amplitude/phase to be represented by ($c_c$, $c_s$)=($a_c \cos(\theta/2) - b_c \sin(\theta/2)$, $a_s \cos(\theta/2) - b_3 \sin(\theta/2)$) at the ($x_c$, $x_s$) coordinates. Here, $\cos^2(\theta/2)$ represents transmittance of the beam splitter for the target light and is set to a value approximated to 1 to maximally transmit the target light (at this time, because $\sin^2(\theta/2)$ becomes a value approximated to zero, $b_c$ and $b_s$ are set to very large values). For this reason, ($b_c$, $b_s$) is set, so that any position shifts can be performed for the $x_c$ axis and the $x_s$ axis. A graph 731 represents a state of the interference light after performing the interference, such that the amplitude/phase of the interference light in the case in which a defect is absent becomes the original point. By performing the position shifts, identification performance of the presence or absence of the defect can be improved as compared with the homodyne detection or the heterodyne detection. A graph 732 represents a state of the interference light after performing the interference, such that the amplitude/phase of the interference light in the case in which a defect is absent is slightly shifted from the original point. Thereby, identification performance can be improved as compared with the case of the graph 731 (which will be described below with reference to FIG. 9). A graph 733 represents a state of light in the case in which the interference is performed using light of a squeezed state, not a coherent state, or squeezing is performed after the interference. The light of the state other than the coherent state is used, so that a portion between a region 761 in the case in which a defect is absent and a region 762 in the case in which a defect is present is expanded. As a result, the fluctuation with respect to the amplitude can be further suppressed and quantum noise can be suppressed.

In order to make the state of the interference light become a state illustrated in FIG. 7C, it is necessary to control the amplitude and the phase of the reference light. In addition, instead of a detector such as a general photodiode in which the photon number cannot be counted, a detector that can count the photons is necessary. If the photon count is performed on the interference light of the coherent state represented by the point ($c_c$, $c_s$) on the phase space representation, a detected photon number follows a Poisson distribution having an average $\lambda = c_c^2 + c_s^2$. Because the dispersion of the Poisson distribution is $\lambda$, the fluctuation of the detected photon number can be suppressed when ($c_c$, $c_s$) becomes close to the original point (in particular, in a coherent state which is called a vacuum state and in which $c_c=c_s=0$ is satisfied, the fluctuation is not generated and the detected photon number becomes zero at all times). For this reason, as compared with the target light of FIG. 7B, the strength of the interference light is decreased as illustrated in FIG. 7C, so that the quantum noise can be suppressed. In the homodyne detection or the heterodyne detection, generally, the interference is performed such that the amplitude of the light after the interference greatly increases. In this case, because an average photon number greatly increases, it is difficult to perform the photon count. In addition, even though the photon count is performed, the fluctuation greatly increases due to the above-described cause.

In FIG. 7C, the interference is performed such that the amplitude of the interference light in the case in which a defect is absent decreases. However, the interference may be performed such that the amplitude of the interference light in the case in which a defect is present decreases.

Figure 9:
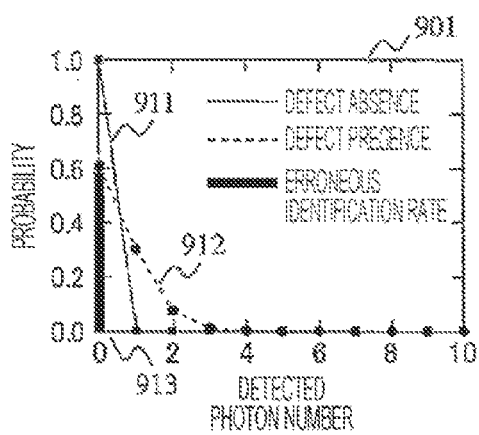
FIG. 9 is a graph illustrating a probability distribution regarding a detected photon number in the first embodiment.
Figure 9:
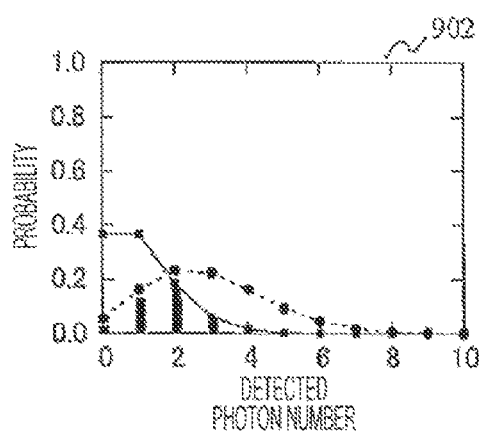

FIG. 9 is a graph illustrating a probability distribution regarding the detected photon number in this embodiment. Graphs 901 and 902 illustrate probability distributions regarding the detected photon numbers in the case in which the states of the interference light are represented by the graphs 731 and 732 in FIG. 7C, respectively. In this embodiment, in the graph 731, the amplitudes in the case in which a defect is absent and the case in which a defect is present are set as 0.0 and 0.7, respectively. In addition, in the graph 732, the shift amounts are changed such that the amplitudes in the individual cases increase by 1.0 and the amplitudes are set as 1.0 and 1.7, respectively. In order to simplify the description, here, it is assumed that both prior probabilities P (defect absence) and P (defect presence) with respect to the defect absence and the defect presence are ½ (that is, it is assumed that an inspection place where a defect is absent and an inspection place where a defect is present appear at the same probability). A solid line 911 and a broken line 912 illustrate conditional probability distributions P (n|defect absence) and P (n|defect presence) regarding detected photon numbers n in the case in which a defect is absent and the case in which a defect is present, respectively. In the individual graphs, the detected photon number follows the Poisson distribution having the average of the square of the amplitude, as described above. Therefore, in the graph 901, in the conditional probability in the case in which it is assumed that a defect is absent, the probability of the detected photon number being 0 becomes 1.0 and the other probabilities become 0.0. Meanwhile, in the conditional probability in the case in which it is assumed that a defect is present, the probability of the detected photon number being 0 becomes about 0.60 and the probability of the detected photon number being 1 becomes about 0.31. The conditional probability distribution becomes a distribution in which the probability decreases as the detected photon number increases. In addition, in the graph 902, in the conditional probability in the case in which it is assumed that a defect is absent, the probability of the detected photon number being 0 or 1 becomes about 0.39. The conditional probability distribution becomes a distribution in which the probability decreases as the detected photon number increases. Meanwhile, in the conditional probability in the case in which it is assumed that a defect is present, the probability of the detected photon number being 2 becomes about 0.21 to be a maximum value. The conditional probability distribution becomes a distribution in which the probability decreases even though the detected photon number increases or decreases.

The defect identifier determines the presence or absence of the defect, on the basis of the detected photon number. In this embodiment, when an appropriate threshold value T is used and the detected photon number is T or more, the defect identifier identifies the presence or absence of the defect as the defect presence and when the detected photon number is less than T, the defect identifier identifies the presence or absence of the defect as the defect absence. In the graph 901, in the case of T=1, an average erroneous identification rate (the probability of a defect identification result being wrong) is minimized and in the graph 902, in the case of T=2, the average erroneous identification rate is minimized. The erroneous identification rate includes both an erroneous detection rate (the probability of the case in which a defect is absent being identified as the defect presence) and a defect undetected rate (the probability of the case in which a defect is present being identified as the defect absence). In the graphs 901 and 902, erroneous identification rates (conditional probabilities) with respect to individual detected photon numbers in the cases of T=1 and T=2 are illustrated by bar graphs. Values that are obtained by multiplying values obtained by integrating values illustrated by the bar graphs with an entire detected photon number with the prior probability of ½ become entire erroneous identification rates and become about 0.31 and 0.24, respectively (for example, in the graph 901, the erroneous detection rate is obtained by adding the probability of being identified as the defect presence when the detected photon number n is 0 to the probability of being identified as the defect absence when the detected photon number n is 1 or more (If this is represented by an expression, P(n≥1|defect absence)×P(defect absence)+P(n=0|defect presence)×P(defect presence)≈0×0.5+0.62×0.5=0.31 is obtained). As such, instead of the amplitude in the case in which a defect is absent being set to zero as illustrated by the graph 731, the amplitude is slightly shifted from the zero as illustrated by the graph 732, so that the average erroneous identification rate can be decreased.

In this embodiment, the threshold value is set to the detected photon number and the presence or absence of the defect is identified. However, the present invention is not limited thereto. For example, in an actual inspection environment, the probability distribution for the detected photon number may not follow the simple Poisson distribution frequently, like when types of defects cannot be specified. In this case, superior identification may not be performed in only a simple threshold process. As an example of identification more complex than the threshold process, a method of identifying the presence or absence of the defect as the defect presence in the case in which when the probability distribution of the defect presence for each detected photon number is more than the probability distribution of the defect absence and identifying the presence or absence of the defect as the defect absence in the other cases may be used. In addition, when light of a plurality of wavelengths is radiated and the photon count is performed for light of each wavelength, instead of individually performing the identification for a detected photon number of the light of each wavelength, the identification may be performed collectively using information of detected photon numbers for the plurality of wavelengths.

Figure 8:
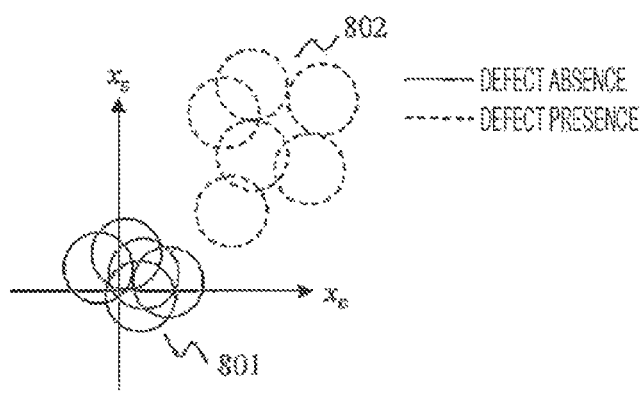
FIG. 8 is a diagram representing a state of interference light according to the first embodiment by a phase space representation.

FIG. 8 is a diagram representing a state of the interference light by the phase space representation, similar to FIG. 7C. However, in both the case in which a defect is absent and the case in which a defect is present, the state of the light includes the uncertainty due to a factor other than the quantum noise and the state is fluctuated more complexly. In the case in which a defect is absent, variableness of the state of the interference light due to an unevenness degree of a sample surface or noise is exemplified as a factor of the fluctuation. In addition, in the case in which a defect is present, if the sizes or the shapes of the defects represented by 711 and 712 are different, the state of the target light generally becomes different. Therefore, the state of the interference light also becomes different. However, even when the state of the interference light is fluctuated more uncertainly, an influence of the quantum noise can be suppressed by a method of performing the photon count after performing the interference such that the strength of the interference light decreases.

As described above, according to this embodiment, in at least one of the case in which a defect is absent and the case in which a defect is present, the interference is performed such that the amplitude of the light after the interference is smaller than the amplitude of the target light. As a result, in the photon measurement, the erroneous identification rate due to the quantum noise decreases and superior defect detection performance can be obtained.

Second Embodiment

Figure 2:
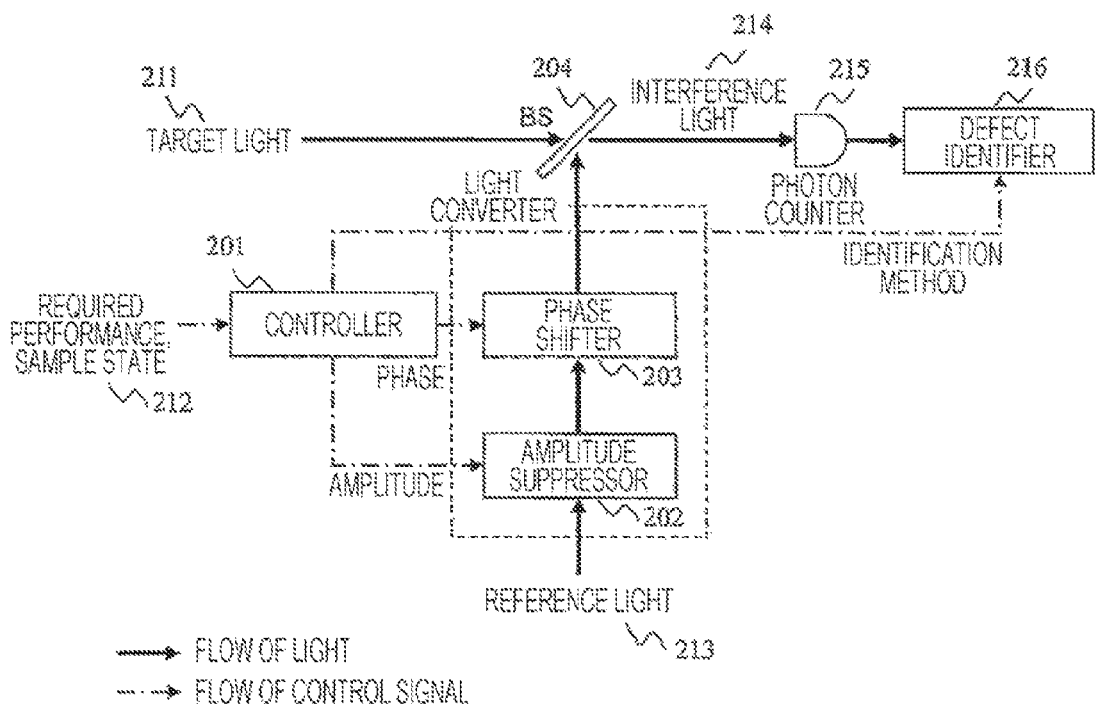
FIG. 2 is a structural diagram of an optical inspection apparatus according to a second embodiment.

An optical inspection apparatus according to a second embodiment of the present invention will be described using FIG. 2. After an amplitude/phase of reference light 213 is changed to an appropriate amplitude/phase by an amplitude suppressor 202 and a phase shifter 203, the reference light 213 is caused to interfere with target light 211 by a beam splitter 204 and interference light 214 is obtained. At this time, as described below with reference to FIGS. 10A and 10B, because an optimal amplitude/phase of the reference light 213 is different according to required performance and a sample state, an amplitude suppression amount and a phase shift amount are adjusted by a controller 201 according to the required performance and the sample state. In addition, the controller 201 may control an identification method of a defect identifier 216. The required performance represents information of required sensitivity of defect detection (a defect size), a throughput, a type of a defect set as a detection target, an erroneous identification rate, an erroneous detection rate (the probability of identifying the case in which a defect is absent as defect presence), and a defect undetected rate (the probability of identifying the case in which a defect is present as defect absence). In addition, the sample state represents information of a surface unevenness degree, reflectance, a sample thickness, and a material in the case in which a defect is absent and the case in which a defect is present.

Figure 3:
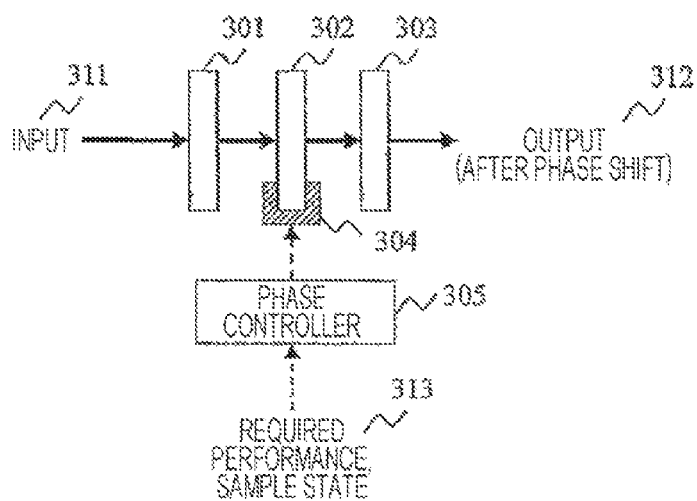
FIG. 3 is a structural diagram of a phase shifter according to the second embodiment.

FIG. 3 illustrates a phase shifter according to this embodiment that changes a phase shift amount of light. First, after light 311 input to the phase shifter is incident on a ¼ wavelength plate 301, light transmitted therefrom is sequentially incident on a ½ wavelength plate 302 and a ¼ wavelength plate 303. Light transmitted from the ¼ wavelength plate 303 becomes output light 312 of the phase shifter. The three wavelength plates 301 to 303 are made of an anisotropic material. In addition, each wavelength plate has a cylindrical shape and light passes through a center axis thereof. The input light is assumed as polarized light. In this configuration, if the ½ wavelength plate is rotated, a phase of the input light is shifted according to an angle with a polarization direction of the input light. Therefore, a rotator 304 to rotate the ½ wavelength plate is provided. The rotator 304 is controlled by a phase controller 305 according to required performance or a sample state 313, so that a phase of the light can be changed.

The phase shifter that changes the phase shift amount of the light may have a configuration different from the configuration according to the embodiment illustrated in FIG. 3. For example, a method using a liquid crystal modulator, a method using an MEMS modulator, and a method using a variable delay optical path may be used.

Figure 18:
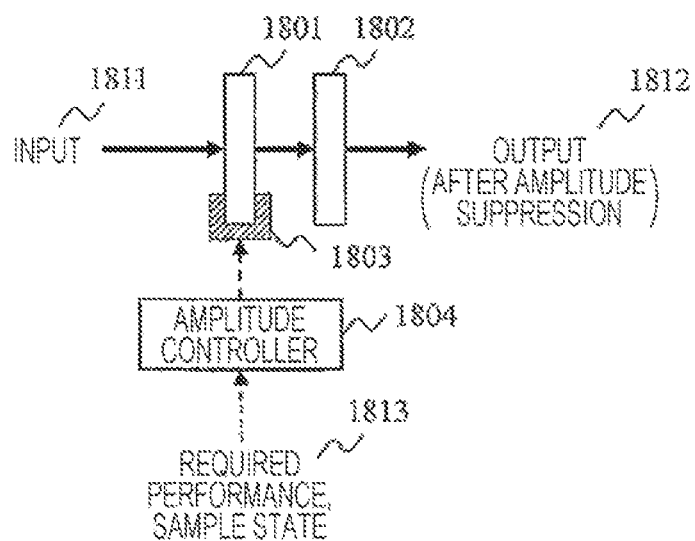
FIG. 18 is a structural diagram of an amplitude suppressor according to the second embodiment.

FIG. 18 illustrates an amplitude suppressor according to this embodiment that changes an amplitude suppression amount of light. First, after light 1811 input to the phase suppressor is incident on a polarization plate 1801, light transmitted therefrom is incident on a polarization plate 1802 and transmission light thereof becomes output light 1812 of the amplitude suppressor. Each of the polarization plates 1801 and 1802 has a cylindrical shape and light passes through a center axis thereof. The input light is polarized in a 0° direction and the polarization plates 1801 and 1802 transmit polarized light of φ and 0° directions, respectively. At this time, transmittance of each of the polarization plates 1801 and 1802 becomes $\cos^2 \phi$. For this reason, the output light is in a polarization state of 0° equal to a polarization state of the input light, but amplitude thereof is suppressed to $\cos^4 \phi$ times. Therefore, a rotator 1803 to rotate the polarization plate 1801 is provided. The rotator is controlled by an amplitude controller 1804 according to the required performance or the sample state, so that an amplitude suppression amount of light can be adjusted. In this embodiment, the amplitude suppressor using the two polarization plates has been described. However, the present invention is not limited thereto.

Figure 10A:
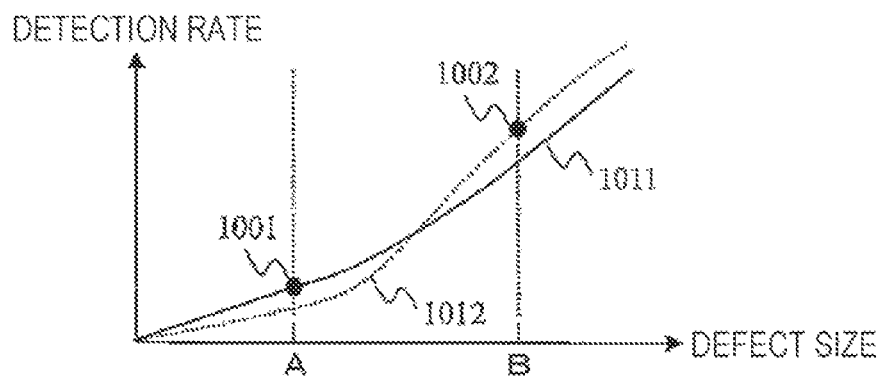
FIG. 10A is a graph schematically illustrating a relation of a defect size and a detection rate according to the second embodiment.

FIG. 10A is a graph schematically illustrating a relation of a defect size and a detection rate. A horizontal axis represents the defect size and a vertical axis represents the detection rate. The conditions (the strength of radiation light and the like) other than the defect size are the same. In general, because an amount of target light increases when the defect size increases, a high detection rate can be obtained. Graphs 1011 and 1012 illustrate performances in the case in which an amplitude/phase of reference light, an amplitude/phase of radiation light, and an identification method in a defect identifier are adjusted to allow detection rates to be maximally obtained, when defect sizes are A and B, respectively. When the defect sizes are A and B, detection rates illustrated by points 1001 and 1002 are obtained. If the amplitude/phase of the reference light is not adjusted, performances illustrated by the points 1001 and 1002 cannot be achieved. Meanwhile, the required defect size is different according to a purpose. For example, high-sensitivity detection to detect a defect having the size A may be necessary and detection of a defect having a size larger than the size B may be necessary.

Figure 10B:
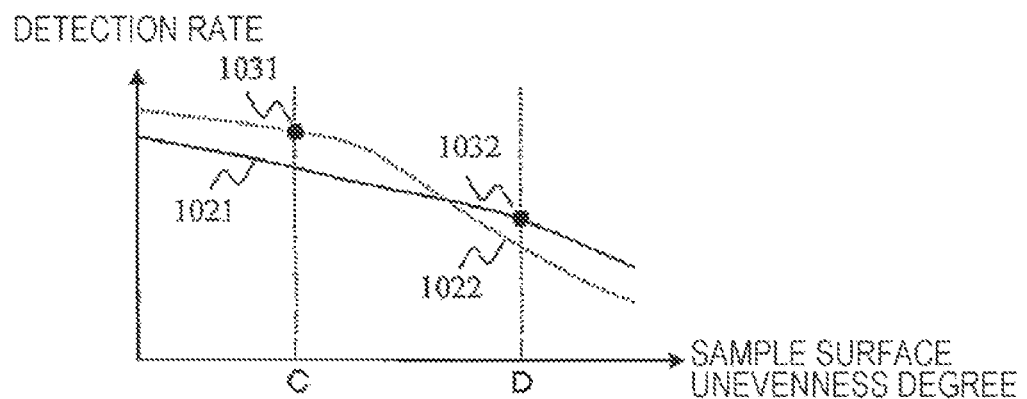
FIG. 10B is a graph schematically illustrating a relation of sample surface unevenness and a detection rate according to the second embodiment.

FIG. 10B is a graph schematically illustrating a relation of a sample surface unevenness degree and a detection rate. The sample surface unevenness degree is a degree representing a number or a size of sample surface unevenness per unit area. A horizontal axis represents a surface unevenness degree and a vertical axis represents a detection rate. Similar to FIG. 10A, the conditions other than the surface unevenness are the same. Because noise increases when the surface unevenness degree increases, the detection rate increases when the surface unevenness degree decreases. Graphs 1021 and 1022 illustrate performances in the case in which an amplitude/phase of reference light and an identification method in a defect identifier are adjusted to allow detection rates to be maximally obtained, when sample surface unevenness degrees are C and D, respectively. Similar to the case of FIG. 10A, an optimal detection rate cannot be obtained for each surface unevenness degree as long as the amplitude/phase of the reference light is not adjusted.

Therefore, in this embodiment, in a light interference device or a defect identifier, at least one of the amplitude of the reference light, the phase of the reference light, amplitude of radiation light radiated by a light source, and a phase of the radiation light is changed according to at least one of the required performance of the defect detection and the sample state. An optimal inspection method to enable the quantum noise to be suppressed is different according to the required performance of the defect detection and the sample state. For this reason, in this embodiment, according to a required value, the radiation light or the reference light is adjusted or the defect identification method is adjusted, so that an appropriate inspection can be performed. The same trade-off relation as FIG. 10A or 10B is realized with respect to other required performance such as the required throughput or the sample state and superior performance can be obtained by the same adjustment.

Figure 16:
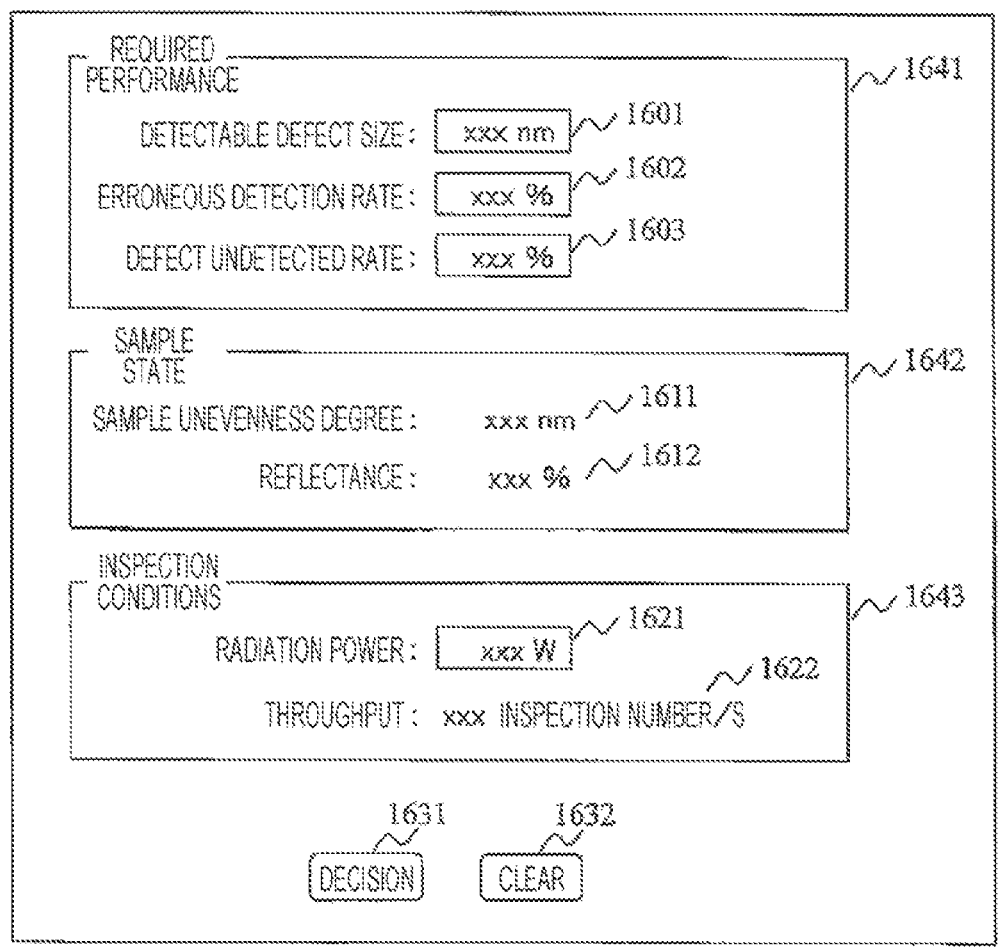
FIG. 16 is a diagram illustrating an interface screen according to the second embodiment.

FIG. 16 illustrates an interface screen according to this embodiment to demand an input of the required performance, the sample state, and the inspection conditions or display them. This screen includes a required performance display region 1641, a sample state display region 1642, an inspection condition display region 1643, a decision button 1631, and a clear button 1632. In the required performance display region 1641, a text box 1601 to demand an input of a detectable defect size as information regarding a defect set as a detection target is present. In addition, text boxes 1602 and 1603 to demand inputs of an erroneous detection rate and a defect undetected rate as information regarding defect detection performance are present. In addition, in the sample state display region 1642, a region 1611 representing a sample unevenness degree as information regarding a sample state and a region 1612 representing reflectance as the information regarding the sample state are present. These values may be calculated by performing an evaluation to investigate the sample state in advance. In the screen, results thereof may be only displayed and an input may be requested for a user. In the inspection condition display region 1643, a text box 1621 to demand an input of radiation power is present. In addition, a region 1622 to display the throughput is present. The throughput is calculated using the required performance, the sample state, and other inspection condition and a result thereof is displayed. Instead of calculating the throughput, the throughput may be input from the user and other value (for example, the erroneous detection rate) may be automatically computed.

According to the interface screen of FIG. 16, an inspection in which a necessary value of the z required performance and the sample state is input from the user, the amplitude/phase of the radiation light or the reference light or the defect identification method is adjusted according to the value thereof, and the quantum noise is appropriately suppressed according to the required value can be performed.

Figure 17:
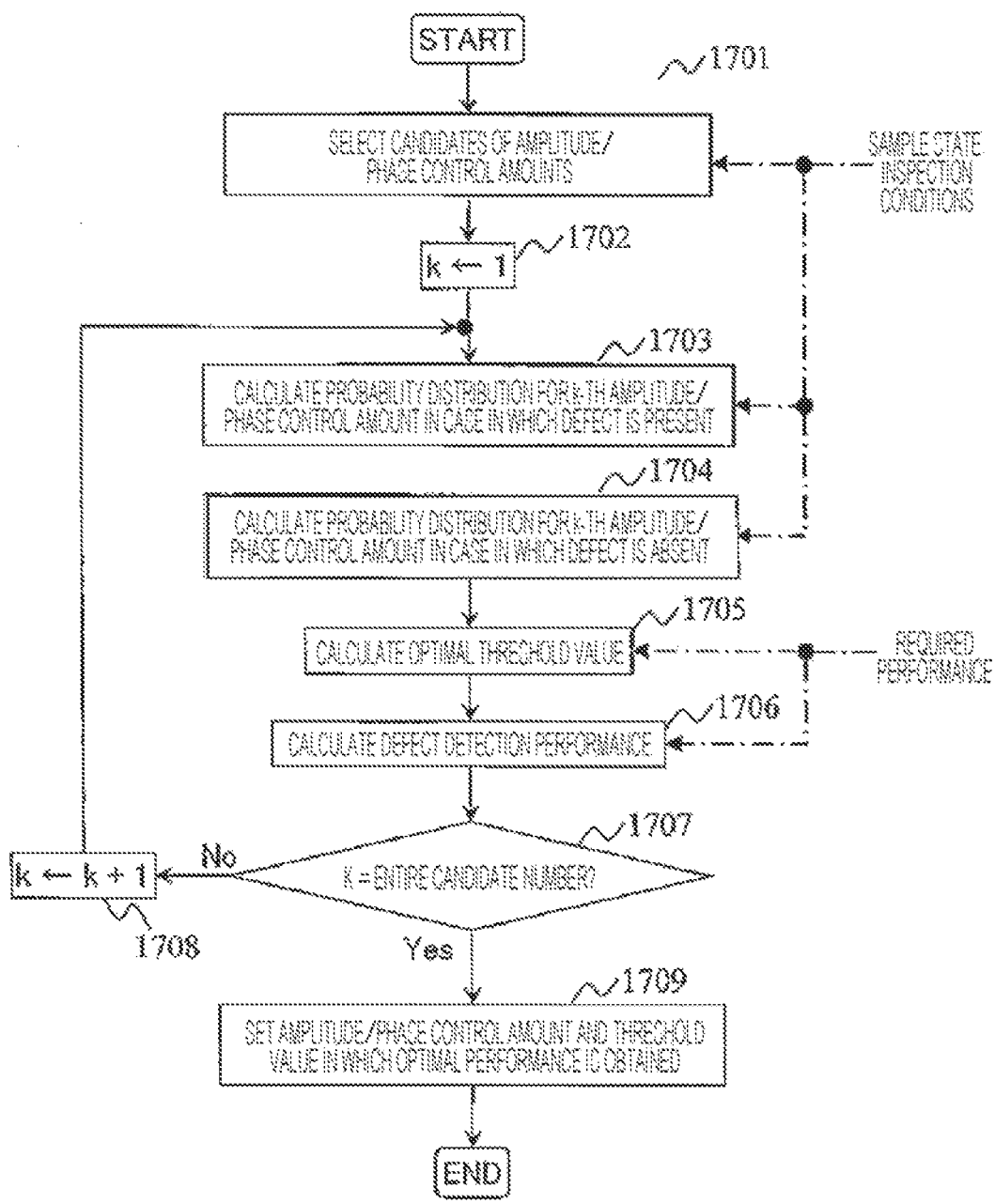
FIG. 17 is a diagram illustrating a process flow according to the second embodiment.

FIG. 17 illustrates a process flow according to this embodiment to adjust the amplitude/phase of the radiation light or the reference light or the defect identification method, according to the required performance, the sample state, and the inspection conditions. First, in a process 1701, candidates of control amounts with respect to the amplitude/phase are selected. Specifically, the candidates are selected from the control amounts in which the amplitude of the interference light in the case in which a defect is absent becomes a value approximated to zero, by considering the phase space representation described in FIG. 7C. By maximally arranging average phases of the interference light in the case in which a defect is absent and the case in which a defect is present, superior detection performance is generally obtained. Therefore, the candidates are selected from the conditions in which the phases are arranged. Next, in a process 1702, 1 is substituted for k (a variable representing the repetitive number of times). In processes 1703 and 1704, probability distributions in the case in which a defect is present and the case in which a defect is absent are calculated with respect to a k-th amplitude/phase control amount representing a k-th candidate, respectively (as a result of these processes, the graph illustrated in FIG. 9 is drawn). In the processes 1701, 1703, and 1704, information of the sample state or the inspection conditions can be used. Next, in a process 1705, an optimal threshold value is calculated on the basis of the probability distribution and in a process 1706, defect detection performance in the case of using the optimal threshold value is calculated. In the processes 1705 and 1706, information of the required performance can be used. Next, in a process 1707, it is investigated whether k is equal to the entire number of candidates selected by the process 1701. When k is not equal to the entire number of candidates, 1 is added to k in a process 1708 and the processes 1703 to 1707 are repeated. When k becomes equal to the entire number of candidates, in a process 1709, the amplitude/phase control amount and the threshold value in which the optimal performance is obtained, among all of the candidates, are set.

In the process 1705, some criteria such as a method of minimizing an average erroneous identification rate and a method of setting a constant defect undetected rate and minimizing an erroneous detection rate are considered as evaluation criteria to calculate the optimal threshold value. However, the criterion suitable for an inspection purpose may be selected. In addition, the user may be caused to select the criterion through the interface screen illustrated in FIG. 16. In this embodiment, the method based on the threshold value has been described as the defect identification method. However, the present invention is not limited to the above-described method.

As described above, according to this embodiment, the amplitude suppression amount and the phase shift amount are adjusted according to the required performance and the sample state, so that a superior detection rate can be obtained according to the required performance and the sample state.

Third Embodiment

An optical inspection apparatus according to a third embodiment of the present invention will be described using FIGS. 4A and 4B. In an embodiment of FIG. 4A, light generated by a light source 401 is divided by a beam splitter 402 and one of divided parts is radiated to a sample by a sample radiator 403 and the other is used as reference light. After an amplitude/phase of the reference light is controlled by an amplitude suppressor 404 and a phase shifter 405, the reference light is caused to interfere with target light by a beam splitter 406 and light after the interference is input to a photon counter 407. FIG. 4B illustrates another embodiment. Similar to FIG. 4A, the light generated by the light source 401 is used in both the radiation light and the reference light. However, a phase shifter 411 performs a phase shift on the radiation light, not the reference light. Because a value in which a phase difference of the target light and the reference light is intended at the time of the interference may be used, the phase of the reference light does not need to be shifted and the phase of the radiation light may be shifted as illustrated in FIG. 4B or the phase of the target light may be shifted. Likewise, the amplitude control may be performed on the radiation light.

According to this embodiment, the light generated by the light source is divided into the two parts and one is radiated to the sample and the other is used as the reference light. As a result, the amplitude difference and the phase difference of the target light and the reference light are easily controlled as compared with the case of using different light sources.

Fourth Embodiment

An optical inspection apparatus according to a fourth embodiment of the present invention using squeezed light will be described using FIGS. 6A and 6B. In this embodiment, reference light or interference light is squeezed in a light interference device. Similar to the embodiment described in FIGS. 4A and 4B, in this embodiment, light generated by a light source is divided into two parts and one is radiated to a sample and the other is used as reference light.

Figure 4A:
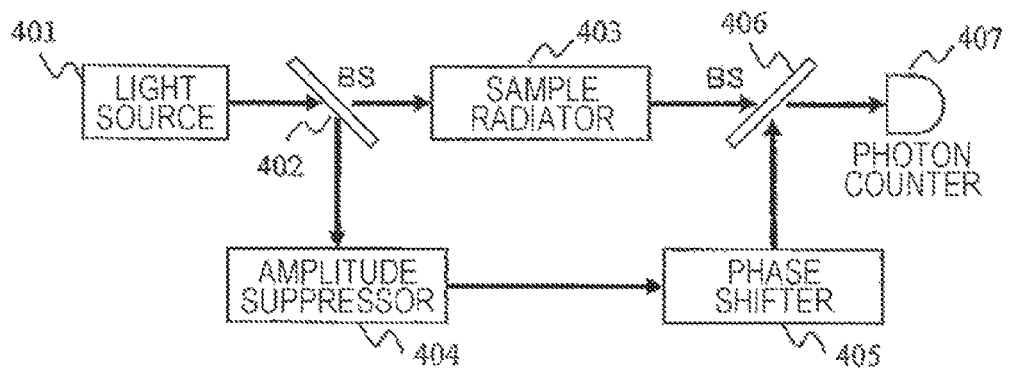
FIG. 4A is a structural diagram of an optical inspection apparatus according to a third embodiment.
Figure 4B:
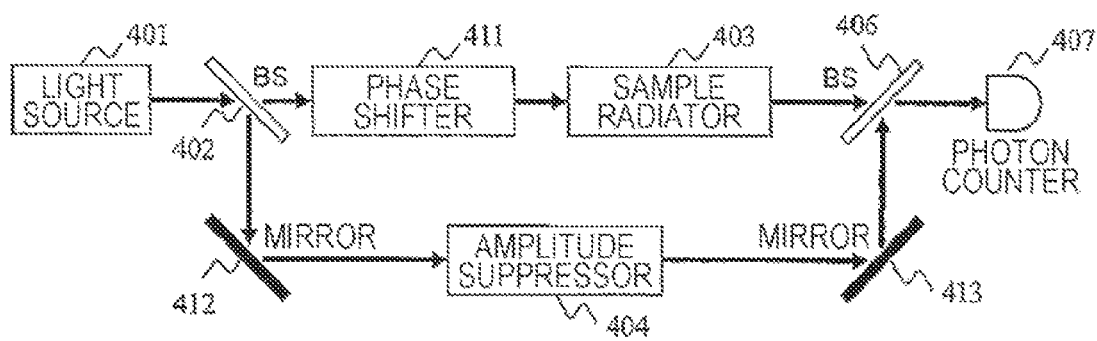
FIG. 4B is a structural diagram of an optical inspection apparatus according to a modification of the third embodiment.
Figure 6A:
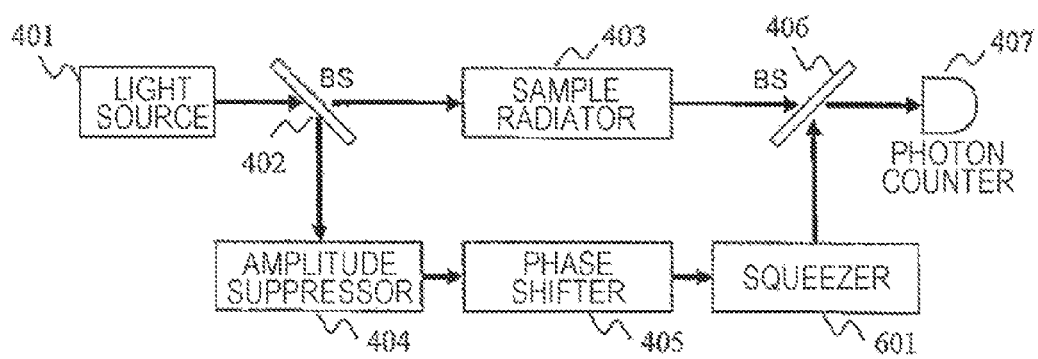
FIG. 6A is a structural diagram of an optical inspection apparatus according to a fourth embodiment.
Figure 6B:
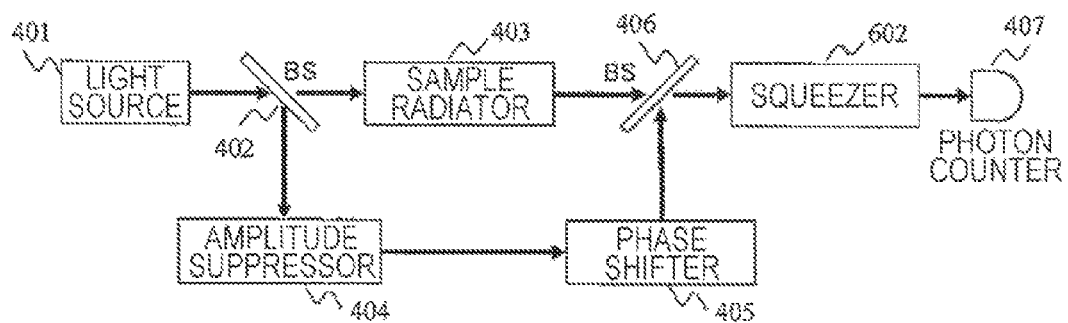
FIG. 6B is a structural diagram of an optical inspection apparatus according to a modification of the fourth embodiment.

A configuration illustrated in FIG. 6A is similar to the configuration illustrated in FIG. 4A. However, a squeezer 601 performs squeezing on the reference light after a phase thereof is controlled by a phase shifter 405. A configuration illustrated in FIG. 6B is also similar to the configuration illustrated in FIG. 4A. However, a squeezer 602 performs squeezing on the interference light.

If the squeezing is performed, as described by the graph 733, in the phase space representation, the magnitude of the fluctuation can be made to become anisotropic on the $x_c$ and $x_s$ axes and the fluctuation for the amplitude of the interference light can be further suppressed.

Because the strength of the reference light is sufficiently large and can be adjusted, the amplitude control of the reference light is easily performed even though squeezing is performed on the reference light, as illustrated in FIG. 6A. In addition, as illustrated in FIG. 6B, when the interference light having the low strength is a target, it is necessary to perform the squeezing after the strength of the light is maximally maintained. However, because distortion at the time of propagation is generally large in light of a squeezed state as compared with light of a coherent state, as illustrated in FIG. 6B, if the photon count can be performed immediately after the squeezing, an influence of the distortion can be decreased.

According to this embodiment, the squeezed light is used, so that the magnitude of the fluctuation for the detected photon number can be controlled as compared with the case of using coherent light to be laser light from a light source. Therefore, the quantum noise can be further suppressed as compared with the first to third embodiments.

Fifth Embodiment

Figure 11A:
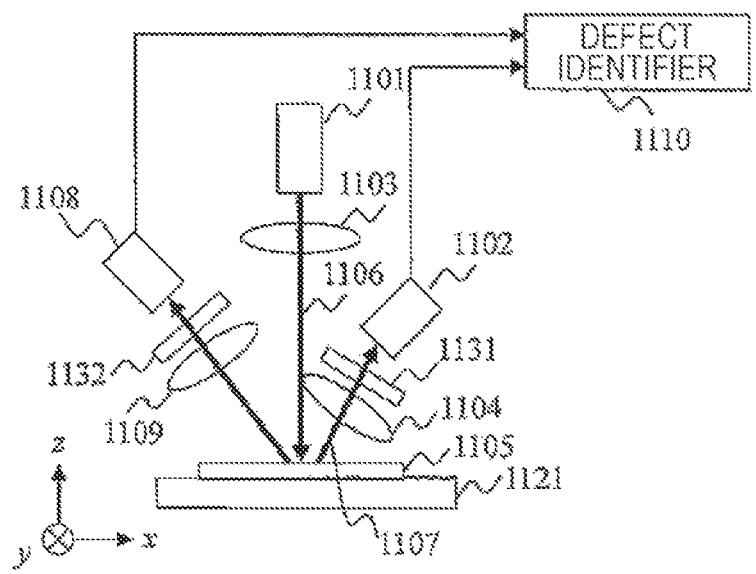
FIG. 11A is a structural diagram of an optical inspection apparatus according to a fifth embodiment.
Figure 11B:
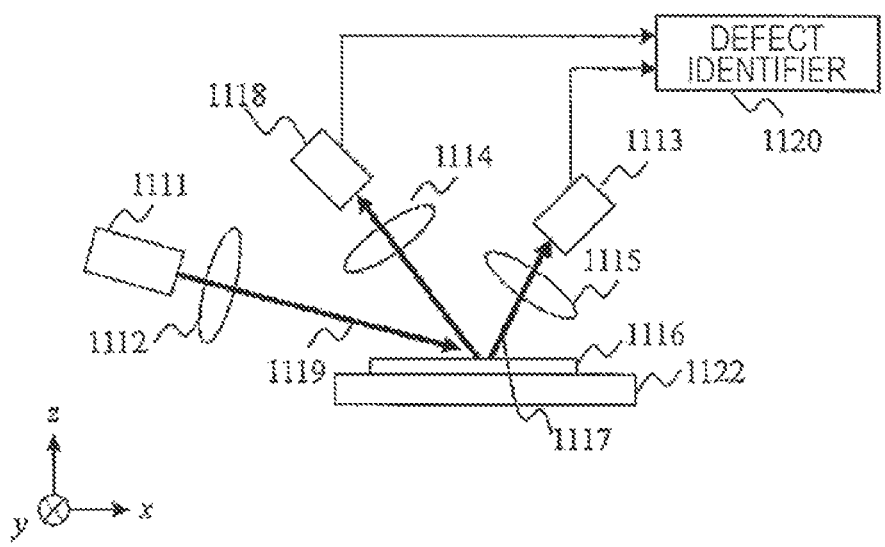
FIG. 11B is a structural diagram of an optical inspection apparatus according to a modification of the fifth embodiment.

An optical inspection apparatus according to a fifth embodiment of the present invention will be described using FIGS. 11A and 11B. In FIG. 11A, a light source 1101 radiates light to a sample 1105 vertically from the upper side. The light is condensed on the sample by a lens 1103. The light from the sample is condensed by a lens 1104 and is input to a receiver 1102. The receiver 1102 includes a light interference device and a photon counter. A plurality of receivers may be included. For example, the receivers may be arranged to receive scattered light or reflected light of a direction different from a direction of light 1107, like a lens 1109 and a receiver 1108. The presence or absence of a defect is identified by a defect identifier 1110 using detected photon numbers to be output of the receivers 1102 and 1108. The sample 1105 is arranged on a stage 1121 and the stage 1121 is moved in xy directions, so that a light radiation position on the sample can be controlled. Polarization elements 1131 and 1132 may be placed on front steps of the receivers 1102 and 1108 and scattered light generated from minute unevenness in a sample surface may be suppressed to facilitate identification with scattered light from a defect. In FIG. 11B, a configuration similar to the configuration illustrated in FIG. 11A is illustrated. However, a light source 1111 is arranged such that light is radiated to a sample 1116 from an oblique direction, not a vertical direction. The light from the light source 1111 is condensed on a sample by a lens 1112.

According to this embodiment, light is condensed on the sample, the photon count is performed on light from a light condensing position using one or more receivers, and the presence or absence of the defect is identified on the basis of the detected photon number in each receiver. Therefore, scattered light from different angles can be detected and a defect can be detected with higher precision.

Sixth Embodiment

Figure 12A:
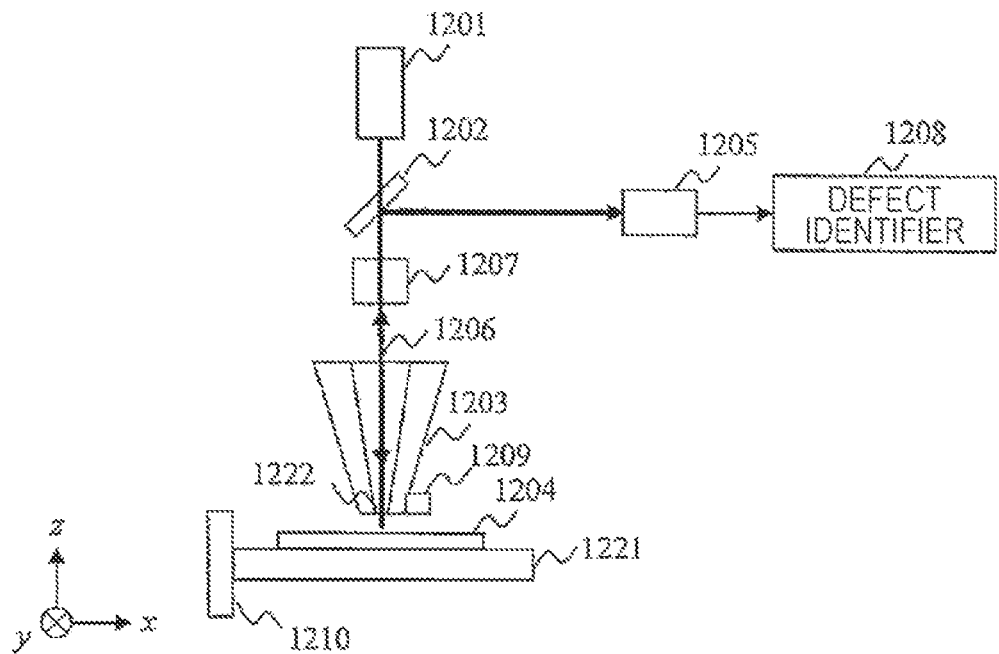
FIG. 12A is a structural diagram of an optical inspection apparatus according to a sixth embodiment.

An optical inspection apparatus according to a sixth embodiment of the present invention will be described using FIGS. 12A and 12B. In FIG. 12A, a light source 1201 radiates light to a sample 1204. The light from the light source 1201 is input to a near-field light generator 1203 and the near-field light generator 1203 emits near-field light from a front edge 1222 thereof. The near-field light generator 1222 is approached to the sample 1204, until the near-field light arrives at the sample. Scattered light or reflected light from the sample passes through the same optical path 1206 as radiation light, is reflected by a beam splitter 1202, and is input to a receiver 1205. The beam splitter 1202 transmits the radiation light from the light source 1201 and reflects the light from the sample. This can be realized by polarizing the light from the light source, arranging a ¼ wavelength plate 1207 on the optical path, and configuring the beam splitter 1202 by a polarized beam splitter. The receiver 1205 includes a light source of reference light, a light interference device, and a photon counter. The presence or absence of a defect is identified by a defect identifier 1208 using a detected photon number to be an output of the receiver 1205. The sample 1204 is arranged on a stage 1221 and the stage 1221 is moved in xy directions, so that a light radiation position on the sample can be controlled.

Figure 12B:
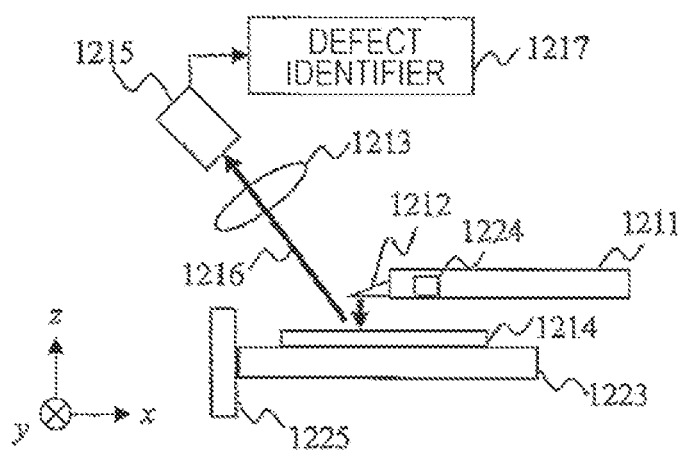
FIG. 12B is a structural diagram of an optical inspection apparatus according to a modification of the sixth embodiment.

FIG. 12B is a diagram illustrating a modification of this embodiment in which the near-field light is radiated to the sample. A near-field light generator 1203 includes a near-field head 1212 and a near-field head supporting portion 1211 and the near-field head 1212 is approached to a sample 1214, until near-field light emitted from a front edge thereof arrives at the sample. Scattered light or reflected light from the sample is condensed by a lens 1213 and is input to a receiver 1215. As compared with the configuration of FIGS. 11A and 11B, the configuration of FIGS. 12A and 12B is used, so that the light can be condensed on a narrow region on the sample. Therefore, scattered light or reflected light from a minute defect can be obtained with high strength.

In FIG. 12A, a height measuring device 1209 is further provided and measures the relative height of the near-field light generator 1203 and the surface of the sample 1204. A stage height adjustor 1210 adjusts the height of the stage 1221 according to a measurement result to maintain the relative height of the near-field light generator 1222 and the surface of the sample 1204 at a constant value. Similar to the above case, in FIG. 12B, a height measuring device 1224 and a stage height adjustor 1225 are provided and the relative height of the near-field head 1212 and the surface of the sample 1214 is adjusted to be maintained at a constant value. Similar to the fifth embodiment, polarization elements may be placed on front steps of the receivers 1205 and 1215 and scattered light or reflected light generated from minute unevenness in a sample surface may be suppressed to facilitate identification with scattered light or reflected light from a defect.

In this embodiment, the optical path lengths of the radiation light and the target light are adjusted by adjusting the height of the sample and the phases of the target light and the reference light are arranged. However, instead of the height of the sample, relative positions of components (for example, a mirror, a beam splitter, a polariscope, and the like) in the optical inspection apparatus may be adjusted. By the position adjustment, instead of adjusting the optical path lengths of the target light and the reference light, the optical path length of only the reference light may be adjusted. In addition, the phases of the target light and the reference light may be directly adjusted using a phase shifter, according to the relative position of the sample, and the phases of the target light and the reference light may be arranged. As such, the phases of the target light and the reference light are adjusted by a phase adjusting unit (the stage height adjustor 1203, an adjusting unit of the relative positions of the components in the optical inspection apparatus, and the phase shifter) and the phases are arranged, so that a defect can be detected with higher precision.

As described above, according to this embodiment, the near-field light is used, so that scattered light or reflected light from a minute defect can be obtained with high strength. In addition, the relative height of the same surface and the near-field light generator 1203 (the front edge 1222 or the near-field head 1212) is detected and feedback is applied, so that the phases of the target light and the reference light can be arranged. In a method of radiating different light to a sample to be described below using a ninth embodiment, when reflectance of the sample is greatly changed, it is difficult to stabilize amplitude of the reference light. Meanwhile, as in this embodiment, the method of adjusting the relative height is used, so that the reference light of the stabilized amplitude can be obtained, even when it is difficult to obtain the reference light of the stabilized amplitude as in the method according to the ninth embodiment.

Seventh Embodiment

Figure 13:
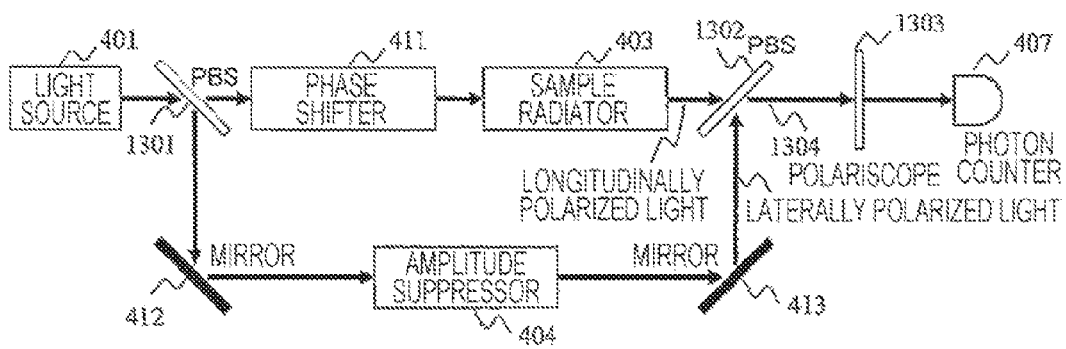
FIG. 13 is a structural diagram of an optical inspection apparatus according to a seventh embodiment.

An optical inspection apparatus according to a seventh embodiment of the present invention will be described using FIG. 13. As compared with the configuration illustrated in FIG. 4B, in a configuration according to this embodiment, polarized beam splitters (in the drawings, referred to as PBS) 1301 and 1302 to be one type of beam splitters are used as the beam splitters. Target light and reference light input to the polarized beam splitter 1302 become polarization states orthogonal to each other. In the polarized beam splitter 1302, the target light is completely transmitted and the reference light is completely reflected. As a result, an output 1304 of the polarized beam splitter 1302 can be used as light including the target light and the reference light of which the polarization states are orthogonal to each other. The light is input to a polariscope 1303 to cause the target light and the reference light to interfere with each other. If a polarization angle of the target light is set as 0° and a polarization angel of the reference light is set as 90° and it is assumed that light of a polarization angle θ is transmitted in the polariscope 1303, transmittances of the target light and the reference light become $\cos^2 θ$ and $\sin^2 θ$, respectively, by the polariscope 1303. Therefore, θ is set as a value approximated to zero to minimize a decrease in the strength of the target light. In addition, the amplitude/phase of the reference light or the radiation light is controlled according to the set θ. When light reflected from the polariscope results in adverse effect, the target light may be input to the polariscope at some shifted angle, not vertically.

During propagation of light, noises are overlapped and become a factor of an S/N decrease, similar to the quantum noise. If the reference light and the target light are made to pass through almost the same optical path, during the propagation of the light, the same noises are overlapped in the reference light and the target light. For this reason, a difference of the reference light and the target light is taken by the interference, so that an influence of the overlapped noises can be decreased. Therefore, in FIG. 13, the optical path length between the polarized beam splitters 1301 and 1302 is configured to become sufficiently short. Thereby, during the propagation of the light, both the influence of the overlapped noises and the quantum noise can be decreased. At this time, it is necessary to execute a process using the reference light and the target light as different light, until the target light and the reference light interfere with each other. However, the polarization states are made to be orthogonal to each other, so that the light can be separated by the polarized beam splitter as in this embodiment. By using the polariscope, two lights of which polarized states are orthogonal to each other can be made to interfere with each other.

As described above, according to this embodiment, the reference light and the target light are made to pass through the same optical path and the influence of the noise is decreased. As a result, defect identification performance can be improved.

Eighth Embodiment

Figure 14:
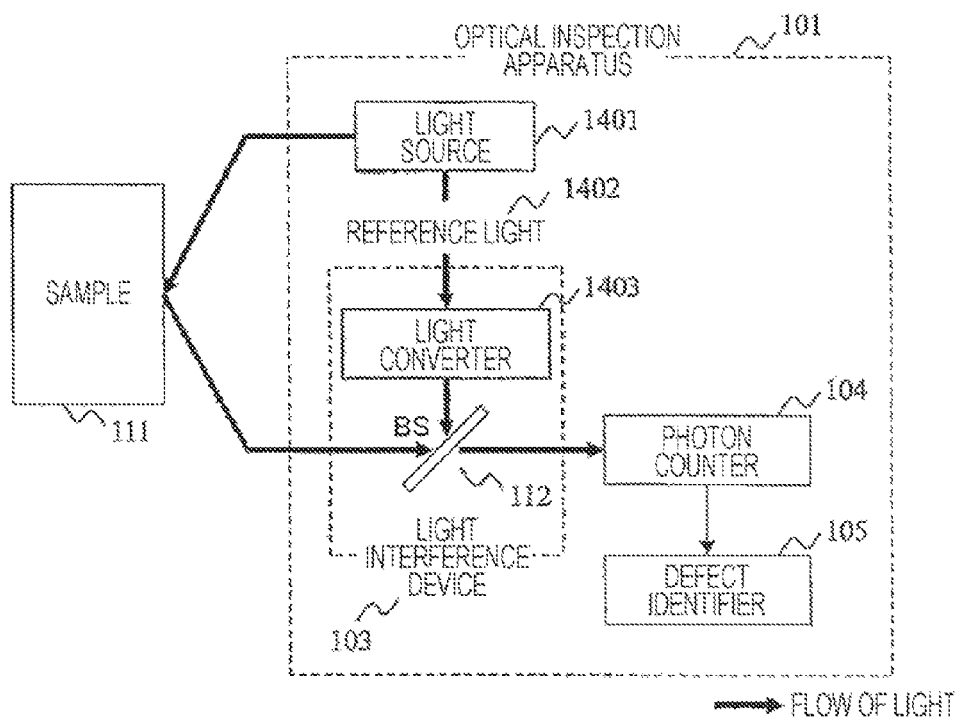
FIG. 14 is a structural diagram of an optical inspection apparatus according to an eighth embodiment.

An optical inspection apparatus according to an eighth embodiment of the present invention will be described using FIG. 14. The same configurations as the first embodiment are denoted by the same reference numerals and explanation thereof is omitted. In this embodiment, at the same time as radiating light from a light source 1401 to a sample 111, reference light 1402 is generated. The light radiated to the sample and the reference light are generated from a single light source. After the amplitude/phase of the reference light 1402 is controlled by a light converter 1403, the reference light is made to interfere with target light by a beam splitter 112.

According to this embodiment, the light generated from the single light source is used in both the light radiated to the sample and the reference light, so that phases of both the light can be easily arranged as compared with the case of using different light sources. As a result, quantum noise can be suppressed and defect identification performance can be improved.

Ninth Embodiment

Figure 15:
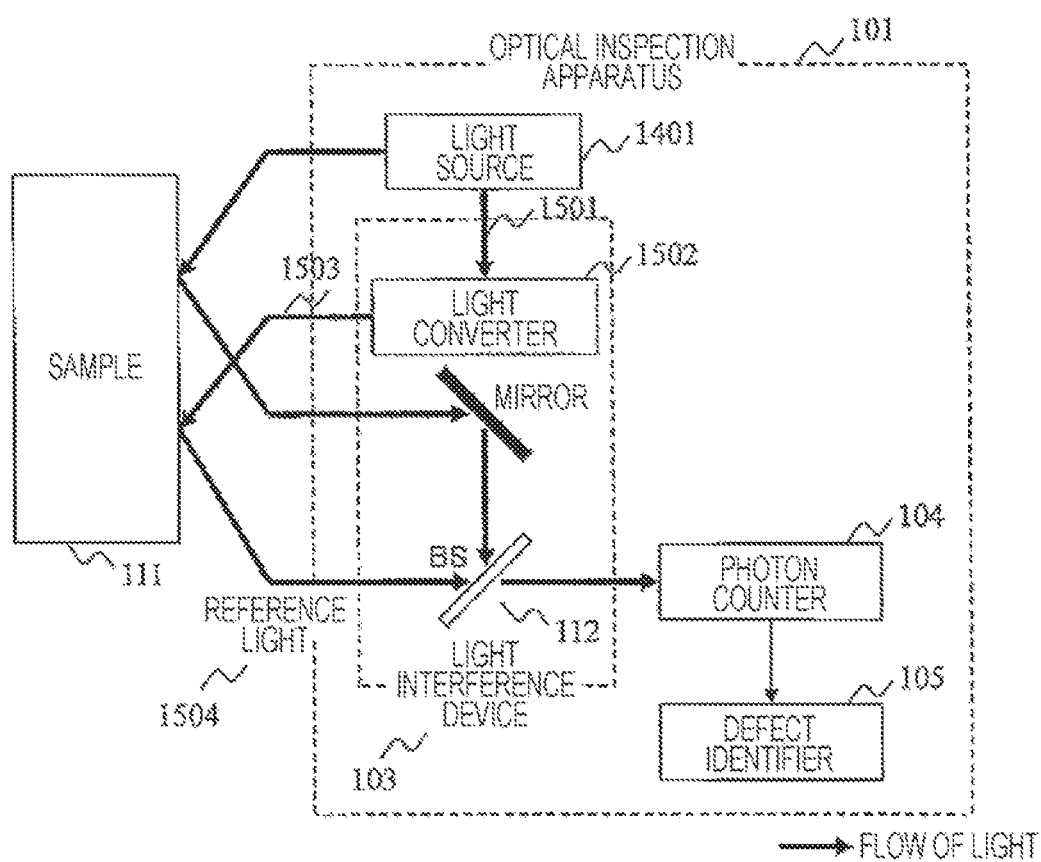
FIG. 15 is a structural diagram of an optical inspection apparatus according to a ninth embodiment.

An optical inspection apparatus according to a ninth embodiment of the present invention will be described using FIG. 15. As compared with the configuration illustrated in the eighth embodiment, instead of using light 1501 generated by a light source 1401 as reference light, light 1504 obtained from a sample after controlling the amplitude/phase of the light 1501 by a light converter 1502 and radiating the light to the sample is used as the reference light.

Phases of the target light and the reference light need to be arranged with high precision. However, because a sample surface is not flat and has unevenness in general, an optical path length of the light radiated to the sample changes according to the unevenness of the sample surface. Therefore, as a method of arranging the phases, light different from radiation light is radiated to a surrounding position and light transmitted, scattered, or reflected from the sample with respect to the light radiated to the different position is used as the reference light, as in this embodiment.

According to this embodiment, even when large unevenness is present on the sample surface, the optical path length of the reference light changes according to the change of the optical path length of the target light. Therefore, the phases can be stably arranged and defect identification performance can be improved.

Tenth Embodiment

Figure 21:
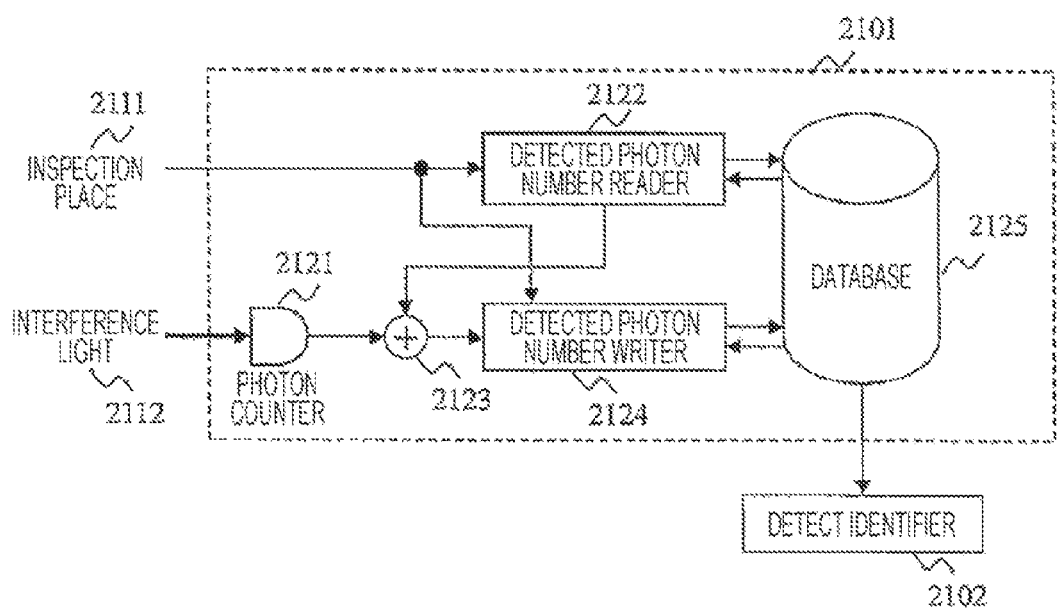
FIG. 21 is a structural diagram of an optical inspection apparatus according to a tenth embodiment.

An optical inspection apparatus according to a tenth embodiment of the present invention will be described using FIG. 21. FIG. 21 illustrates a photon counter 2101 and a defect identifier 2102. In order to realize high efficiency of an inspection, light may be radiated to a wide region of a sample and an inspection may be performed while a light radiation area is gradually changed. In this case, light may be radiated to the same place several times. At this time, a sum of detected photon numbers in individual inspection places can be stored in a database 2125 by a configuration of the photon counter 2101. Specifically, a photon count result when the light is radiated in the past is read by a detected photon number reader 2122. In addition, the photon count is performed on interference light 2112 by a photon counter 2121. A sum of a photon count result and the past photon count result is computed by an adder 2123 and a result thereof is written to the database 2125 by a detected photon number writer 2124. By repeating the above process, a sum of detected photon numbers obtained by individual light radiation when the plurality of times of light radiation are performed on the same place can be stored in the database 2125. In the defect identifier 2102, the presence or absence of a defect is identified using a value read from the database. In the photon counter 2121, a line sensor may be used. In this case, an inspection place 2111 includes information of a plurality of places.

According to this embodiment, the sum of the detected photon numbers obtained by the individual light radiation when the plurality of times of light radiation are performed on the same place is stored in the database 2125, so that a wide region can be inspected with high efficiency and high precision.

The present invention is not limited to the embodiments described above and various modifications are included in the present invention. For example, the embodiments are described in detail to facilitate the description of the present invention and are not limited to embodiments in which all of the described configurations are included.

REFERENCE SIGNS LIST

101 optical inspection apparatus
102 light source
103 light interference device
104 photon counter
105 defect identifier
106 light converter
111 sample
112 beam splitter
113 reference light
201 controller
202 amplitude suppressor
203 phase shifter
204 beam splitter
211 target light
212 required performance/sample state
213 reference light
214 interference light
215 photon counter
216 defect identifier
301 to 303 wavelength plate
304 rotator
305 phase controller
311 input light of phase shifter
312 output light of phase shifter
313 required performance/sample state
401 light source
402 beam splitter
403 sample radiator
404 amplitude suppressor
405 phase shifter
406 beam splitter
407 photon counter
411 phase shifter
412, 413: mirror

The invention claimed is:

1. An optical inspection apparatus, comprising:
   a light source which radiates light to a sample;
   a light interference device configured to generate transmitted, scattered, or reflected target light from the sample and a reference light to interfere with each other, such that a strength of light after the interference becomes lower than a strength of the target light;
   a photon counter configured to count a number of photons in the light after the interference by the light interference device; and
   a defect identifier which calculates a probability distribution of each case in which a defect is present or absent, and identifies the presence or absence of a defect, on the basis of a detected photon number obtained by the photon counter and the calculated probability distributions, wherein
   a controller controls the amplitude and the phase of the reference light based on a required performance parameter threshold, wherein the controller is configured to manipulate a quarter wavelength plate and a half wavelength plate located in the reference arm, so as to provide a decreased average erroneous identification rate in case the defect is present and decreased average erroneous identification rate in case the defect is absent.

2. The optical inspection apparatus according to claim 1, wherein the photon counter uses any one of a plurality of Geiger mode/avalanche photodiodes, a plurality of photomultipliers, and a multi-pixel photon counter.

3. The optical inspection apparatus according to claim 1, wherein the light interference device changes at least one of amplitude and a phase of the target light or the reference light, according to at least one of required performance of defect detection and a sample state.

4. The optical inspection apparatus according to claim 1, wherein the defect identifier changes an identification method, according to at least one of required performance of defect detection and a sample state.

5. The optical inspection apparatus according to claim 1, wherein a part of the light generated by the light source is radiated to the sample and is used as the target light and other part is used as the reference light.

6. The optical inspection apparatus according to claim 1, wherein the light source generates another light to radiate a different position from a position of the light radiated to the sample to obtain the target light and the light interference device uses the other light transmitted, scattered, or reflected from the sample at the different position as the reference light and causes the reference light to interfere with the target light.

7. An optical inspection method, comprising:
   a light radiation step of radiating light to a sample;
   a light interference step of causing target light transmitted, scattered, or reflected from the sample and a reference light to interfere with each other, such that a strength of light after the interference becomes lower than a strength of the target light;
   a photon counting step of counting a number of photons in the light after the interference
   a probability distribution calculation step of calculating a probability distribution of each case in which a defect is present or absent;
   a defect identification step of identifying the presence or absence of a defect, on the basis of a detected photon number obtained by the photon counting step and the calculated probability distribution, wherein
   the amplitude and the phase of the reference light are controlled so that: i) an average erroneous identification rate in case the defect is present, and ii) an average erroneous identification rate in case the defect is absent, are decreased.

8. The optical inspection method according to claim 7, wherein, in the photon count step, any one of a plurality of Geiger mode/avalanche photodiodes, a plurality of photomultipliers, and a multi-pixel photon counter is used.

9. The optical inspection method according to claim 7, wherein, in the light interference step, at least one of amplitude and a phase of the target light or the reference light is changed according to at least one of required performance of defect detection and a sample state.

10. The optical inspection method according to claim 7, wherein, in the defect identification step, an identification method is changed according to at least one of required performance of defect detection and a sample state.

11. The optical inspection method according to claim 7, wherein, in the light interference step, a magnitude of an amplitude fluctuation of the reference light or the light after the interference is suppressed.

12. The optical inspection method according to claim 7, wherein, in the light radiation step, a part of light is radiated to the sample and other part is used as the reference light.

13. The optical inspection method according to claim 7, wherein, in the light radiation step, another light is radiated to a position different from a position of the light radiated to the sample to obtain the target light and, in the light interference step, the another light is transmitted, scattered, or reflected from the sample at the different position is used as the reference light.

14. The optical inspection method according to claim 7, further comprising:
    a near-field generation step of generating near-field light from the light source, by a near-field light generator.

15. The optical inspection method according to claim 14, further comprising:
    a phase adjustment step of adjusting phases of the target light and the reference light.

16. The optical inspection method according to claim 7, wherein the defect identification is performed in parallel using a line sensor, and the photon counting is performed after the interference with the reference light in which amplitude and phase have been controlled, to suppress an influence of quantum noise.

* * * * *